(12) United States Patent
Choudary et al.

(10) Patent No.: US 6,387,033 B1
(45) Date of Patent: May 14, 2002

(54) PREPARATION OF NEW LAYERED DOUBLE HYDROXIDES EXCHANGED WITH OSMATE FOR ASYMMETRIC DIHYDROXYLATION OF OLEFINS TO VICINAL DIOLS

(75) Inventors: Boyapati Manoranjan Choudary; Naidu Sreenivasa Chowdari; Mannepalli Lakshmi Kantam; Kondapuram Vijaya Raghavan; Chinta Venkat Reddy Reddy, all of Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/721,510

(22) Filed: Nov. 22, 2000

(51) Int. Cl.⁷ .................................................. C07C 31/18
(52) U.S. Cl. ........................ 561/852; 423/594; 423/599; 423/600; 423/593; 568/853; 568/860
(58) Field of Search ................................ 423/593, 594, 423/599, 600; 568/852, 853, 860

(56) References Cited

U.S. PATENT DOCUMENTS

| | | | | |
|---|---|---|---|---|
| 3,879,523 A | * | 4/1975 | Miyata et al. | 423/593 X |
| 4,049,583 A | * | 9/1977 | Lauder | 423/593 X |
| 4,217,291 A | * | 8/1980 | Wu et al. | 423/593 X |
| 4,413,151 A | | 11/1983 | Michaelson et al. | 568/860 |
| 5,260,461 A | | 11/1993 | Hartung et al. | 549/447 |
| 5,684,159 A | | 11/1997 | O'Brien et al. | 548/452 |
| 5,691,263 A | * | 11/1997 | Park et al. | 502/306 X |

* cited by examiner

*Primary Examiner*—Paul F. Shaver
(74) *Attorney, Agent, or Firm*—Darby & Darby

(57) ABSTRACT

LDH-osmate of the formula $[M^{II}_{(1-x)}M^{III}_x(OH)_2][OsO_4^{2-}]_{x/2} \cdot zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and $M^{III}$ is a trivalent ion selected from the group consisting of $Al^{3+}$, $Cr^{3+}$, $Mn^{3+}$, $Fe^{3+}$ and $Co^{3+}$, and x is the mole fraction having integral value ranging from 0.2 to 0.33, and z is the number of water molecules and ranges from 1 to 4, useful as, a catalyst, and a process for the preparation thereof and use thereof to manufacture vicinal diols.

10 Claims, No Drawings

US 6,387,033 B1

PREPARATION OF NEW LAYERED DOUBLE HYDROXIDES EXCHANGED WITH OSMATE FOR ASYMMETRIC DIHYDROXYLATION OF OLEFINS TO VICINAL DIOLS

FIELD OF THE INVENTION

The present invention relates to preparation of layered double hydroxides exchanged with osmate (LDH-osmates) useful as recyclable catalysts for preparing vicinal diols. More particularly the present invention relates to preparation of layered double hydroxides exchanged with osmate of the formula $[M^{II}_{(1-x)}M^{III}_x(OH)_2][OsO_4^{2-}]_{x/2} \cdot zH_2O$ wherein $M^{II}$ is a divalent cation ($Mg^{2+}$, $Mn^{2+}$, $Fe^{2+}$, $Co^{2+}$, $Ni^{2+}$, $Cu^{2+}$, $Zn^{2+}$ or $Ca^{2+}$); $M^{III}$ is a trivalent ion ($Al^{3+}$, $Cr^{3+}$, $Mn^{3+}$, $Fe^{3+}$, $Co^{3+}$ or $Ni^{3+}$), x is the mole fraction having integral value ranging from 0.2 to 0.33, and z is the number of water molecules and ranges from 1 to 4; and methods of preparation and use thereof. The LDH-osmates of this invention are recyclable catalysts for preparing vicinal diols by asymmetric dihydroxylation (AD) of olefins in presence of cinchona alkaloid compounds.

BACKGROUND OF THE INVENTION

This invention particularly relates to an eco-friendly process employing recyclable LDH-osmates as heterogeneous catalysts in place of soluble osmium catalysts for preparing vicinal diols by asymmetric dihydroxylation of olefins in presence of cinchona alkaloid compounds. The dihydroxylated products are important intermediates for the preparation of drugs and pharmaceuticals. For example the products of cinnamic acid esters are intermediates for taxol side chain, an anticancer drug, diltiazem, calcium antagonist and chloramphenicol, an antiboitic. Propranolol, a β blocker can also be derived from the diol obtained through this method.

There are serious disadvantages in performing the catalytic AD reaction with homogeneous system in the manufacture of vicinal diols due to presence of toxic remnants of osmium in products and high cost of osmium tetroxide or potassium osmate dihydrate. By employing the heterogeneous catalytic system, the cost naturally comes down due to easy recovery and recyclability of the catalyst for number of recycles and very insignificant loss of osmium tetroxide, when compared with homogenous system. The products thus obtained using heterogeneous catalyst system are benign in the sense that the presence of osmium in minor impurities in the dihydroxylated products is also precluded.

Reference is made to U.S. Pat. Nos. 4,871,855 and 5,260,421 wherein asymmetric dihydroxylation of olefins are carried by osmium tetroxide and cinchona alkaloids in homogeneous way. The inherent disadvantages in this process are cumbersome procedure for the recovery of the osmium catalyst from the reaction mixture, generation of toxic waste and possibility of presence of toxic osmium in traces in the product.

Reference is made to U.S. Pat. No. 5,516,929 wherein asymmetric dihydroxylation of olefins are carried by osmium tetroxide and polymer-bound cinchona alkaloids in heterogeneous way. The drawbacks are difficulty in quantitative recovery of toxic osmium catalyst, lower enantioselectivity and reduction in activity and enantioselectivity in each and every recycle experiments.

Reference is made to U.S. Pat. No. 5,968,867 wherein asymmetric dihydroxylation of olefins are carried by osmium tetroxide and silicagel supported bis-cinchona alkaloid derivatives in heterogeneous way. The drawbacks are difficulty in quantitative recovery of toxic osmium catalyst and reduction in activity and enantioselectivity in each and every recycle experiments.

Reference is made to European patent EP 940,170 A2 wherein catalytic asymmetric dihydrpxylation of alkenes are carried by using a polymer-supported osmium tetroxide catalyst. The drawbacks are requiring higher amount of catalyst (5 mol %/), longer reaction time and use of expensive polymer as a support.

OBJECTS OF THE INVENTION

The main object of the present invention is to prepare a heterogeneous recyclable LDH-osmates and to use in catalytic amounts for preparing vicinol diols by asymmetric dihydroxylation of olefins employing oxidants in presence of cinchona alkaloid compounds which obviates the drawbacks as detailed above.

Another object of the present invention is LDH as synthesized having interstitial anions such as chloride, nitrate, carbonate, sulfate or calcination of LDH having the said interstitial anions at temperatures in the range of 350 to 550° C. are used as precursors for the preparation of LDH-osmates.

Still another object of the present invention is to recover the heterogeneous LDH-osmates used in asymmetric dihdroxylation by simple filtration and reuse for number of cycles with consistent activity and enantioselectivity.

Still another object of the present invention is the quantity of LDH-osmate used in the reaction is 0.01 to 3 mol % of osmium with respect to the substrate.

Still another object of the present invention is wherein the co-oxidant is N-methylmorpholine N-oxide (NMO), trimethylamine N-oxide, hydrogen peroxide, t-butyl hydrogen peroxide, potassium ferricyanide, sodium periodate or molecular oxygen.

Still another object of the present invention is the chiral ligand is monomeric or polymeric, preferably hydroquinidine 1,4-phthalazinediyl diether ($(DHQD)_2PHAL$), hydroquinidine 2,5-diphenyl-4,6-pyrimidinediyl diether (($(DHQD)_2PYR$), hydroquinidine (anthraquinone-1,4-diyl) diether (($(DHQD)_2AQN$), hydroquinidine acetate (DHQD-OAc), O-(4-chlorobenzoyl) hydroquinidine (DHQD-CLB), hydroquinidine 9-phenanthryl ether (DHQD-PHN), hydroquinidine 4-methyl-2-quinolyl ether (DHQD-MEQ) or the other pseudoenantiomeric forms of these ligands, etc.

SUMMARY OF THE INVENTION

Accordingly, the present invention relates to a LDH-osmate useful as a catalyst having the formula $[M^{II}_{(1-x)} M^{III}_x(OH)_2][OsO_4^{2-}]_{x/2} \cdot zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and $M^{III}$ is a trivalent ion selected from the group consisting of $Al^{3+}$, $Cr^{3+}$, $Mn^{3+}$, $Fe^{3+}$ and $Co^{3+}$, x is the mole fraction having integral value ranging from 0.2 to 0.33, and z is the number of water molecules and ranges from 1 to 4.

In another embodiment, the present invention relates to a process for the preparation of the catalyst LDH-osmate of the formula $[M^{II}_{(1-x)}M^{III}_x(OH)_2][OsO_4^{2-}]_{x/2} \cdot zH_2O$ wherein z is the number of water molecules, the said process comprising reacting potassium osmate of formula $K_2OsO_4 \cdot 2H_2O$ with a LDH of formula $[M^{II}_{(1-x)} M^{III}_x(OH)_2][A^{n-}]_{x/n} \cdot zH_2O$ where $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and $M^{III}$ is a trivalent ion selected from the group consisting of $Al^{3+}$, $Cr^{3+}$, $Mn^{3+}$, $Fe^{3+}$ and $Co^{3+}$, x is the mole fraction having integral value ranging from 0.2 to 0.33, and z is the number of water molecules and ranges from 1 to 4, in an aqueous solvent at a temperature ranging between 20 to 30° C. for a period of 5 to 24 h under the nitrogen atmosphere followed by filtration to obtain the desired catalyst.

In yet another embodiment, the present invention relates to a method for the preparation of vicinal diols using the recyclable catalyst LDH-osmates of the formula $[M^{II}_{(1-x)}M^{III}_{x}(OH)_2][OsO_4^{2-}]_{x/2}.zH_2O$ wherein $M^{II}$ is a divalent cation ($Mg^{2+}$, $Mn^{2+}$, $Fe^{2+}$, $Co^{2+}$, $Ni^{2+}$, $Cu^{2+}$, $Zn^{2+}$ or $Ca^{2+}$); $M^{III}$ is a trivalent ion ($Al^{3+}$, $Cr^{3+}$, $Mn^{3+}$, $Fe^{3+}$ or $Co^{3+}$), x is the mole fraction having integral value ranging from 0.2 to 0.33, and z is the number of water molecules and ranges from 1 to 4, in catalytic amounts by asymmetric dihydroxylation of olefins using standard methods employing an oxidant in the presence of a cinchona alkaloid compound in a solvent selected from water, acetone, acetonitrile, t-butanol or any mixture thereof at a temperature in the range of −20 to +100° C. for a period 0.5 to 24 h, and obtaining the pure product vicinol diol by a conventional method.

In an embodiment of the present invention, a method for the preparation of vicinol diols using the recyclable catalyst LDH-osmates of the formula $[M^{II}_{(1-x)}M^{III}_{x}(OH)_2][OsO_4^{2-}]_{x/2}.zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$; $M^{III}$ is a trivalent ion selected from the group consisting of $Al^{3+}$, $Cr^{3+}$, $Mn^{3+}$, $Fe^{3+}$ and $Co^{3+}$, x is the mole fraction having integral value ranging from 0.2 to 0.33, and z is the number of water molecules and ranges from 1 to 4, in catalytic amounts by dihydroxylation of olefins using standard methods employing an oxidant in a solvent selected from water, acetone, acetonitrile, t-butanol or any mixture thereof at a temperature in the range of −20 to +100° C. for a period 0.5 to 24 h, and obtaining the pure product vicinal diol by conventional method.

In an embodiment of the present invention, the catalyst has an osmium content in the range between 5 to 30%.

In an embodiment of the present invention, LDH as synthesized has interstitial anions such as chloride, nitrate, carbonate, sulfate.

In a further embodiment of the present invention LDH having the said interstitial anions calcined at temperatures in the range of 350 to 550° C. are used as precursors for the preparation of LDH-osmates.

In an embodiment of the present invention, the quantity of LDH-osmate used in the reaction is 0.01 to 3 mol % of osmium content with respect to the substrate.

In an embodiment of the present invention, LDH-osmate is recovered by simple filtration and reused for several cycles with consistent activity.

In another embodiment of the present invention, the solvent selected for the AD reaction is water, acetone, acetonitrile and/or t-butanol, etc.

In yet another embodiment of the present invention, the oxidant used is selected from the known group consisting of N-methylmorpholine N-oxide (NMO), Trimethylamine N-oxide, hydrogen peroxide, t-butyl hydrogen peroxide, potassium ferricyanide, sodium periodate or molecular oxygen.

In still another embodiment of the present invention, the chiral ligand used is selected from the known group consisting of the monomeric or polymeric, preferably $(DHQD)_2PHAL$, $(DHQD)_2PYR$, $(DHQD)_2AQN$, DHQD-OAc, DHQD-CLB, DHQD-PHN, DHQD-MEQ or the other pseudoenantiomeric forms of these ligands, etc.

In still another embodiment of the present invention, the reaction is, preferably, effected at a known temperature, in the range of −20 to +100° C. for a period of 0.5 to 24 h.

In still another embodiment of the present invention, the dihydroxylated products are important intermediates for the preparation of drugs and pharmaceuticals. Products selected from taxol side chain, an anticancer drug, diltiazem, calcium antagonist and chloramphenicol, an antibiotic.

DETAILED DESCRIPTION OF THE INVENTION

The novelty of the present invention lies in the design and preparation of LDH-osmates through simple exchange process for the first time and uses it in catalytic amounts for preparing vicinal diols by asymmetric dihydroxylation of olefins employing oxidants in presence of cinchona alkaloid compounds. Higher yields and enantioselectivities are obtained when LDH-osmate catalysts are used in the asymmetric dihydroxylation of olefins in aqueous organic solvents. Since the dihydroxylated products are important intermediates for the preparation of drugs and pharmaceuticals, this invention which envisages reduction of toxic osmium metal content in these products is timely and appropriate, due to use of heterogeneous catalyst. The consistent activity and enantioselectivity obtained for several cycles in asymmetric dihydroxylation makes the process economical and possible for commercial realisation. Therefore, LDH-osmates are better option for the synthesis of vicinal diols. The use of different metals and in varied compositions used in the preparation of LDH support has no impact on its final form of osmate catalysts with respect to activity and enantioselectivity. Thus this invention offers the best techno-economic route for the synthesis of vicinal diols, intermediates for the preparation of drugs and pharmaceuticals.

LDH-osmate having the formula $[M^{II}_{(1-x)}M^{III}_{x}(OH)_2][OsO_4^{2-}]_{x/2}.zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and $M^{III}$ is a trivalent ion selected from the group consisting of $Al^{3+}$, $Cr^{3+}$, $Mn^{3+}$, $Fe^{3+}$ and $Co^{3+}$, x is the mole fraction having integral value ranging from 0.2 to 0.33, and z is the number of water molecules and ranges from 1 to 4, is useful as a catalyst in the process. The catalyst LDH-osmate of the formula $[M^{II}_{(1-x)}M^{III}_{x}(OH)_2][OsO_4^{2-}]_{x/2}.zH_2O$ is prepared by reacting potassium osmate of formula $K_2OsO_4$ $2H_2O$ with a LDH of formula $[M^{II}_{(1-x)}M^{III}_{x}(OH)_2][A^{n-}]_{x/n}.zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and $M^{III}$ is a trivalent ion selected from the group consisting of $Al^{3+}$, $Cr^{3+}$, $Mn^{3+}$, $Fe^{3+}$ and $Co^{3+}$, x is the mole fraction having integral value ranging from 0.2 to 0.33, and z is the number of water molecules and ranges from 1 to 4, in an aqueous solvent at a temperature ranging between 20 to 30° C. for a period of 5 to 24 h under the nitrogen atmosphere followed by filtration to obtain the desired catalyst.

The vicinal diols are prepared using the recyclable catalyst LDH-osmates of the formula $[M^{II}_{(1-x)}M^{III}_{x}(OH)_2][OsO_4^{2-}]_{x/2}.zH_2O$ wherein $M^{II}$ is a divalent cation ($Mg^{2+}$, $Mn^{2+}$, $Fe^{2+}$, $Co^{2+}$, $Ni^{2+}$, $Cu^{2+}$, $Zn^{2+}$ and $Ca^{2+}$); $M^{III}$ is a trivalent ion ($Al^{3+}$, $Cr^{3+}$, $Mn^{3+}$, $Fe^{3+}$ or $Co^{+}$), x is the mole fraction having integral value ranging from 0.2 to 0.33, and z is the number of water molecules and ranges from 1 to 4, in catalytic amounts by asymmetric dihydroxylation of olefins using standard methods employing an oxidant in the presence of a cinchona alkaloid compound in a solvent selected from water, acetone, acetonitrile and/or t-butanol at a temperature in the range of −20 to +100° C. for a period 0.5 to 24 h, and obtaining the pure product vicinol diol by a conventional method.

The preparation of vicinol diols may also be done using the recyclable catalyst LDH-osmates of the formula $[M^{II}_{(1-x)}M^{III}_{x}(OH)_2][OsO_4^{2-}]_{x/2} \cdot zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$; $M^{III}$ is a trivalent ion selected from the group consisting of $Al^{3+}$, $Cr^{3+}$, $Mn^{3+}$, $Fe^{3+}$ and $Co^{3+}$ in catalytic amounts by dihydroxylation of olefins using standard methods employing an oxidant in a solvent selected from water, acetone, acetonitrile and/or t-butanol at a temperature in the range of −20 to +100° C. for a period 0.5 to 24 h, and obtaining the pure product vicinal diol by conventional method.

The osmium content in the catalyst ranges between 5 to 30%. LDH as synthesized has interstitial anions such as chloride, nitrate, carbonate, sulfate. Calcined LDH having the said interstitial anions at temperatures in the range of 350 to 550° C. may also be used as precursors for the preparation of LDH-osmates. Generally, the quantity of LDH-osmate used in the reaction is 0.01 to 10 mol % of osmium content with respect to the substrate. LDH-osmate is recovered by simple filtration and reused for several cycles with consistent activity.

The solvent selected for the AD reaction is selected from the group consisting of water, acetone, acetonitrile, t-butanol, or any mixture thereof The oxidant used is selected from the group consisting of N-methylmorpholine N-oxide (NMO), Trimethylamine N-oxide, hydrogen peroxide, t-butyl hydrogen peroxide, potassium ferricyanide, sodium periodate or molecular oxygen.

The chiral ligand used is selected from the group consisting of the monomeric or polymeric, preferably $(DHQD)_2PHAL$, $(DHQD)_2PYR$, $(DHQD)_2AQN$, DHQD-OAc, DHQD-CLB, DHQD-PHN, DHQD-MEQ or the other pseudoenantiomeric forms of these ligands. The reaction is, preferably, effected at a known temperature, in the range of −20 to +100° C. for a period of 0.5 to 24 h. The dihydroxylated products are important intermediates for the preparation of drugs and pharmaceuticals. Products selected from taxol side chain, an anticancer drug, diltiazem, calcium antagonist and chloramphenicol, an antibiotic.

Scientific Explanation

In the present invention, LDH-osmates are prepared for the first time and used in catalytic amounts for preparing vicinal diols by asymmetric dihydroxylation of olefins employing oxidants in presence of cinchona alkaloid compounds in a heterogeneous way.

LDH-osmates are prepared by anion exchange method from the LDH containing chloride or nitrate anions. The osmate anions in LDH are responsible for the dihydroxylation activity of the reaction. The activity of LDH-osmate is similar or higher than the homogeneous counter parts. The higher activity is ascribed to the support effect. The large positive electric potential of $OsO_4^{2-}$ LDH surface induces polarization of N→O bond and facilitates oxygen transfer.

Higher yields and enantioselectivities are obtained with LDH-osmate catalysts used in the asymmetric dihydroxylation of olefins in aqueous organic solvents. Since the dihydroxylated products are important intermediates for the preparation of drugs and pharmaceuticals, this invention is timely and appropriate. Therefore, LDH-osmate is a better option for the synthesis of vicinal diols. The LDH-osmate catalysts prepared irrespective of metals used in the preparation of LDH offered good yields and enantioselectivies in presence of cinchona alkaloids. Thus this invention offers the best techno-economic route for the synthesis of vicinal diols, intermediates for the preparation of drugs and pharmaceuticals.

LDH-osmates are prepared as examplified and used in catalytic amounts for preparing vicinal diols by asymmetric dihydroxylation of olefins employing oxidants in presence of cinchona alkaloid compounds in a heterogeneous way as described in the examples.

The following examples are given by way of illustration of the present invention and therefore should not be construed to limit the scope of the invention.

Preparation of Layered Double Hydroxides

EXAMPLE 1

Preparation of $Mg^{2+}/Al^{3+}/Cl$-LDH (Ia)

A mixture of $MgCl_2 \cdot 6H_2O$ (30.49 g. 0.15 mol) and $AlCl_3 \cdot 6H_2O$ (12.07 g. 0.05 mol) was dissolved in 200 mL of deionised water. The resultant aqueous solution was slowly added at 25° C. to 100 mL of NaOH solution at pH 10 while stirring under a nitrogen flow. The pH of the reaction mixture was maintained constantly (~10) by the continuous addition of 2 M NaOH. The suspension thus obtained was stirred overnight under a nitrogen atmosphere at 70° C. The solid product was isolated by filtration, washed thoroughly with deionised water, and dried overnight at 80° C. Decarbonated water was used in all the synthetic steps. $Mg^{2+}/Al^{3+}/Cl^-$ hydrotalcites of the different Mg/Al ratios were also prepared similarly, using appropriate amounts of magnesium chloride hexahydrate and aluminium chloride hexahydrate.

EXAMPLE 2

Preparation of $mg^{2+}/Al^{3+}/NO_3$-LDH (Ib)

The $Mg^{2+}/Al^{3+}/NO_3^-$ hydrotalcite with a Mg/Al ratio of 3:1 was prepared from magnesium nitrate hexahydrate (30.8 g, 0.12 mol) and aluminum nitrate nonahydrate (15.0 g, 0.04 mol) which were dissolved in 100 ml of deionised and decarbonated water. The pH of the solution was adjusted to ~10 by the addition of NaOH (2M). The slurry was stirred for 2 h at room temperature under nitrogen atmosphere and then filtered under nitrogen atmosphere, washed thoroughly and dried under vacuum at 80° C.

EXAMPLE 3

Preparation of $Mg^{2+}/Al^{3+}/CO_3^{2-}$-LDH (Ic)

A mixture of 60.09 g of $Mg(NO_3)_2 \cdot 6H_2O$ (0.234 mol) and 29.31 g of $Al(NO_3)_3 \cdot 9H_2O$ (0.078 mol) in 70 ml distilled water was added to a solution of 28.12 g, 50% aq. NaOH (0.703 mol) and 22.08 g $Na_2CO_3$ (0.41 mol) in 100 ml distilled water. The addition was carried out slowly in a 500 ml flask equipped with a mechanical stirrer and the resultant heavy slurry was heated at 65±5° C. for about 18 h. The slurry was allowed to cool to room temperature, filtered and washed. The solid was then dried and calcined at 450° C. for 6h in airflow.

EXAMPLE 4

Preparation of $Ni^{2+}/Al^{3+}/Cl$-LDH (Id)

A mixture of $NiCl_2 \cdot 6H_2O$ (35.65 g. 0.15 mol) and $AlCl_3 \cdot 6H_2O$ (12.07 g. 0.05 mol) was dissolved in 200 mL of deionised water. The aqueous solution was slowly added at 25° C. to 100 mL of NaOH solution at pH 10 while stirring under a nitrogen flow. The pH was constantly maintained (~10) by the continuous addition of 2 M NaOH. The suspension was stirred overnight under a nitrogen atmosphere at 70° C. The solid product was isolated by filtration, washed thoroughly with deionised water, and dried overnight at 80° C. All synthetic steps were carried out using decarbonated water.

Preparation of LDH-osmates

EXAMPLE 5

Preparation of $(MgAl)LDH-OsO_4^{2-}$(IIa)

1 g of Ia was suspended in 100 ml of a 1.87 mmol (0.688 g) aqueous potassium osmate solution and stirred at 25° C. for 24 h under $N_2$ atmosphere. The solid product is filtered, washed with decarbonated water and vacuum dried. Chemical analysis showed that the product contains 25.6% of osmium. This means that 1.345 mmol of osmium per 1 gram of the product. The release of equivalent amounts of chloride ions were also quantitatively estimated by titration of the combined filtrates with 0.1N $AgNO_3$ solution in presence of $KCrO_4$ indicator.

EXAMPLE 6

Preparation of $(MgAl)LDH-OsO_4^{2-}$(IIb)

1 g of Ib was suspended in 100 ml of a 1.87 mmol (0.688 g) aqueous potassium osmate solution and stirred at 25° C. for 24 h under $N_2$ atmosphere. The solid product was filtered, washed with decarbonated water and vacuum dried. Chemical analysis showed that the product contains 18.4% of osmium. This means that 0.966 mmol of osmium per 1 gram of the product.

EXAMPLE 7

Preparation of $MgAl)LDH-OsO_4^{2-}$(IIc)

1 g of calcined Ic was suspended in 100 ml of 1.87 mmol (0.688 g) aqueous potassium osmate solution and stirred at 25° C. for 24 h under $N_2$ atmosphere. The solid product was filtered, washed with decarbonated water and vacuum dried. Chemical analysis showed that the product contains 19.95% of osmium. This means that 1.048 mmol of osmium per 1 gram of the product.

EXAMPLE 8

Preparation of $(NiAl)LDH-OsO_4^{2-}$(IId)

1 g of Id was suspended in 100 ml of a 1.87 mmol (0.688 g) aqueous potassium osmate solution and stirred at 25° C. for 24 h under $N_2$ atmosphere. The solid product was filtered, washed with decarbonated water and vacuum dried. Chemical analysis showed that the product contains 24.2% of osmium. This means that 1.271 mmol of osmium per 1 gram of the product. The release of equivalent amounts of chloride ions were also quantitatively estimated by titration of the combined filtrates with 0.1N $AgNO_3$ solution in presence of $KCrO_4$ indicator.

Asymmetric Dihydroxylation of Olefins

The asymmetric dihydroxylation reaction of olefins was performed using the following two methods in order to evaluate LDH-osmates of the present invention.

Method I

LDH-osmates of the formula IIa–IId (0.02 eq. wt. of osmium content in the LDH), cinchona alkaloid $(DHQD)_2PHAL$ (0.02 Eq. Wt.) and N-methylmorpholine-N-oxide (1.5 Eq. Wt.) were stirred for 30 min in the mixed solvent of water/acetone/acetonitrile (in the volume ratio of 1:1:1). To this mixture was added an olefin (1.0 Eq. Wt). After the reaction, the LDH-osmate catalyst was filtered off and washed with methanol. The combined filtrates were concentrated under reduced pressure. The chiral ligand was recovered from the aqueous layer after acidification (1N HCl). The concentrated organic layer was purified to afford the corresponding cis-diol by using conventional processes. The yield and the optical purity of the product were determined.

Method II

LDH-osmate of the formula IIa–IId (0.002.about.0.02 Eq. Wt. of osmium content in the LDH), cinchona alkaloid $(DHQD)_2PHAL$ (0.02 Eq. Wt.), potassium ferricyanide ($K_3$ $Fe(CN)_6$, (3.0 Eq. Wt.) and potassium carbonate ($K_2$ $CO_3$, 3.0 Eq. Wt.) were stirred for 30 min in the mixed solvent of tert-butanol/water (in the volume ratio of 1:1). To this mixture was added an olefin (1.0 Eq. Wt). After the reaction, LDH-osmate catalyst was filtered off and washed with methanol. The combined filtrates were concentrated under reduced pressure. The chiral ligand was recovered from the aqueous layer after acidification (1N HCl). The concentrated organic layer was purified to afford the corresponding cis-diol by using conventional processes. The yield and the optical purity of the product were determined.

Catalytic Asymmetric Dihydroxylation of Olefins Using N-methylmorpholine-N-oxide as a co-oxidant

EXAMPLE 9

Catalytic Asymmetric Dihydroxylation Reaction of trans-stilbene by Using LDH-osmate of the Formula IIa LDH-osmate of the formula IIa (0.02 Eq. Wt.), Hydroquinidine 1,4-phthalazinediyl diether $((DHQD)_2PHAL)$ (0.02 Eq. Wt.) and N-methylmorpholine-N-oxide (1.5 Eq. Wt.) were stirred for 30 min in the mixed solvent of water/acetone/acetonitrile (in the volume ratio of 1:1:1). To this mixture was added trans-stilbene (1.0 Eq. Wt) and stirred at room temperature for 6 hours. After the reaction, LDH-osmate catalyst was filtered off and washed with methanol. The combined filtrates were concentrated under reduced pressure. The chiral ligand was recovered from the aqueous layer after acidification (1N HCl). The pure product was obtained by removing the solvent at reduced pressure followed by column chromatography. (R,R)-(+)-1,2-diphenyl-1,2-ethandiol of more than 99.0% of enantiomeric excess was obtained (yield 96%) [ ]$_D$+92.44 (c 1.0, EtOH): e.e.=99.4%

EXAMPLE 10

Catalytic asymmetric dihydroxylation reaction of trans-stilbene by using LDH-osmate of the formula IIa which had been used in Example 9 without further addition of osmate catalyst. The reaction was performed using an identical process as in Example 9. (R,R)-(+)-1,2-diphenyl-1,2-ethandiol of more than 99.0% of enantiomeric excess was obtained (yield 95%) [ ]$_D$+92.90 (c 1.0, EtOH): e.e.=99.9%

EXAMPLE 11

Catalytic asymmetric dihydroxylation reaction of trans-stilbene by using LDH-osmate of the formula IIa which had been used in Example 10 without further addition of LDH-osmate catalyst The reaction was performed by using an identical process as in Example 9. (R,R)-(+)-1,2-diphenyl-1,2-ethandiol of more than 99.0% of enantiomeric excess was obtained (yield 97%) [ ]$_D$+92.16 (c 1.0, EtOH): e.e.=99.1%

EXAMPLE 12

Catalytic asymmetric dihydroxylation reaction of trans-stilbene by using LDH-osmate of the formula IIa which had been used in Example 11 without further addition of LDH-osmate catalyst. The reaction was performed by using an identical process as in Example 9. (R,R)-(+)-1,2-diphenyl-1,2-ethandiol of more than 97.0% of enantiomeric excess was obtained (yield 94%) [ ]$_D$+90.76 (c 1.0, EtOH): e.e.=97.6%

EXAMPLE 13

Catalytic asymmetric dihydroxylation reaction of trans-stilbene by using LDH-osmate of the formula IIa which had been used in Example 12 without further addition of LDH-osmate catalyst. The reaction was performed by using an identical process as in Example 9. (R,R)-(+)-1,2-diphenyl-1,2-ethandiol of more than 99.0% of enantiomeric excess was obtained (yield 96%) [ ]$_D$+92.81 (c 1.0, EtOH): e.e.=99.8%

EXAMPLE 14

Catalytic asymmetric dihydroxylation reaction of trans-stilbene by using LDH-osmate of the formula IIa which had been used in Example 13 without further addition of LDH-osmate catalyst. The reaction was performed by using an identical process as in Example 9. (R,R)-(+)-1,2-diphenyl-1,2-ethandiol of more than 99.0% of enantiomeric excess was obtained (yield 98%) [ ]$_D$+92.25 (c 1.0, EtOH): e.e.=99.2%

EXAMPLE 15

Catalytic asymmetric dihydroxylation reaction of trans-stilbene by LDH-osmate of the formula IIb The reaction was performed by using an identical process as in Example 9. (R,R)-(+)-1,2-diphenyl-1,2-ethandiol of more than 99.0% of enantiomeric excess was obtained (yield 97%) [ ]$_D$+92.34 (c 1.0, EtOH): e.e.=99.3%

EXAMPLE 16

Catalytic asymmetric dihydroxylation reaction of trans-stilbene by using LDH-osmate of the formula IIc The reaction was performed by using an identical process as in Example 9. (R,R)-(+)-1,2-diphenyl-1,2-ethandiol of more than 99.0% of enantiomeric excess was obtained (yield 95%). [ ]$_D$+92.53 (c 1.0, EtOH): e.e.=99.5%

EXAMPLE 17

Catalytic asymmetric dihydroxylation reaction of trans-stilbene by using LDH-osmate of the formula IId The reaction was performed by using an identical process as in Example 9. (R,R)-(+)-1,2-diphenyl-1,2-ethandiol of more than 99.0% of enantiomeric excess was obtained (yield 96%). [ ]$_D$+92.25 (c 1.0, EtOH): e.e.=99.2%

EXAMPLE 18

Catalytic asymmetric dihydroxylation reaction of trans-stilbene by using LDH-osmate of the formula IIa The reaction was performed by using an identical process as in Example 9 except the cinchona alkaloid is DHQD-CLB. (R,R)-(+)-1,2-diphenyl-1,2-ethandiol of more than 98.0% of enantiomeric excess was obtained (yield 92%) [ ]$_D$+91.32 (c 1.0, EtOH): e.e.=98.2%

EXAMPLE 19

Catalytic asymmetric dihydroxylation reaction of styrene by using LDH-osmate of the formula IIa The reaction was performed by using an identical process as in Example 9 except slow addition of olefin with a reaction time of 12 hours. (R)-phenyl-1,2-ethanediol of more than 95.0% of enantiomeric excess was obtained (yield 94%) [ ]$_D$−34.29 (c 1.0, EtOH): e.e.=95.7%

EXAMPLE 20

Catalytic asymmetric dihydroxylation reaction of trans-beta.-methyl styrene by using LDH-osmate of the formula IIa The reaction was performed by using an identical process as in Example 9 except slow addition of olefin with a reaction time of 12 hours. (R,R)-1-phenyl-1,2-propanediol of more than 98.0% of enantiomeric excess was obtained (yield 97%) [ ]$_D$−30.50 (c 1.0, EtOM): e.e.=98.1%

EXAMPLE 21

Catalytic asymmetric dihydroxylation reaction of methyl trans-cinnamate by using LDH-osmate of the formula IIa The reaction was performed by using an identical process as in Example 9 except slow addition of olefin with a reaction time of 12 hours. (2S,3R)-2,3-dihydroxy-3-phenylpropionate of more than 97.0% of enantiomeric excess was obtained (yield 96%) [ ]$_D$−10.46 (c 1.0, CHCl$_3$): e.e.=97.8%

EXAMPLE 22

Catalytic asymmetric dihydroxylation reaction of allyl 1-naphthyl ether by using LDH-osmate of the formula IIa The reaction was performed by using an identical process as in Example 9.1 except slow addition of olefin with a reaction time of 12 hours. 2,3-dihydroxypropyl-1-naphthyl ether of more than 77.0% of enantiomeric excess was obtained (yield 94%) [ ]$_D$+5.18 (c 1.0, CH$_3$OH): e.e.=77.4%

EXAMPLE 23

Catalytic asymmetric dihydroxylation of olefins using potassium ferricyanide as a co-oxidant Catalytic asymmetric dihydroxylation reaction of trans-stilbene by using LDH-osmate of the formula IIa LDH-osmate of the formula IIa (0.02 Eq. Wt.), bis-cinchona alkaloid of the formula (DHQD)$_2$PHAL (0.02 Eq. Wt.), potassium ferricyanide (K$_3$Fe(CN)$_6$,3.0 Eq. Wt.) and potassium carbonate (K$_2$CO$_3$, 3.0 Eq. Wt.) were stirred for 30 min in the mixed solvent of tert-butanol/water (in the volume ratio of 1:1). To this mixture was added trans-stilbene (1.0 Eq. Wt). After a reaction time of 6 hours, LDH-osmate catalyst separated by filtration. After washing with methanol, combined filtrates were concentrated under reduced pressure. The chiral ligand was recovered from the aqueous layer after acidification (1N HCl). The pure product was obtained by removing the solvent at reduced pressure followed by column chromatography. (S-S)-(−)-1,2-diphenyl-1,2-ethanediol of more than 99.0% of enantiomeric excess was obtained (yield 95%). [ ]$_D$+92.90 (c 1.0, EtOH): e.e.=99.9%

EXAMPLE 24

Catalytic dihydroxylation reaction of trans-stilbene by using LDH-osmate of the formula IIa LDH-osmate of the formula IIa (0.02 Eq. Wt.), N-methylmorpholine-N-oxide (1.5 Eq. Wt.) and trans-stilbene (1.0 Eq. Wt) in the mixed solvent of water/acetone/acetonitrile (in the volume ratio of 1:1:1) were stirred at room temperature for 6 hours. After the reaction LDH-osmate catalyst was filtered off and washed with methanol. The combined filtrates were concentrated under reduced pressure. The pure product, 1,2-diphenyl-1, 2-ethandiol was obtained by removing the solvent at reduced pressure followed by column chromatography. (yield 93%). The experimental results in the Examples 9 to 24 were tabulated in Table 1&2.

TABLE 1

Reuse of catalyst IIa for asymmetric dihydroxylation reaction of trans-stilbene

| Ex. No | run | Yield | ee |
|---|---|---|---|
| 9 | 1 | 96 | 99.4 |
| 10 | 2 | 95 | 99.9 |
| 11 | 3 | 97 | 99.1 |
| 12 | 4 | 94 | 97.6 |
| 13 | 5 | 96 | 99.8 |
| 14 | 6 | 98 | 99.2 |

TABLE 2

Catalytic asymmetric dihydroxylation reaction of olefins by using LDH-osmates of the formulas IIa–IId

| Ex. No | Catalyst[a] | Ligand | Olefin | Time | Yield[b] | ee[c] | Config.[d] |
|---|---|---|---|---|---|---|---|
| 15 | IIb | (DHQD)$_2$PHAL | Trans-stilbene | 6 | 97 | 99.3 | RR |
| 16 | IIc | (DHQD)$_2$PHAL | Trans-stilbene | 6 | 95 | 99.5 | RR |
| 17 | IId | (DHQD)$_2$PHAL | Trans-stilbene | 6 | 96 | 99.2 | RR |
| 18 | IIa | DHQD-CLB | Trans-stilbene | 6 | 92 | 98.2 | RR |
| 19 | IIa | (DHQD)$_2$PHAL | Styrene | 12 | 94 | 95.7 | R |
| 20 | IIa | (DHQD)$_2$PHAL | E-Methylstyrene | 12 | 97 | 98.1 | RR |
| 21 | IIa | (DHQD)$_2$PHAL | E-Methylcinnamate | 12 | 96 | 97.8 | 2S, 3R |
| 22 | IIa | (DHQD)$_2$PHAL | Allyl 1-naphthyl ether | 12 | 94 | 77.4 | S |
| 23 | IIa | (DHQD)$_2$PHAL | Trans-stilbene | 6 | 95 | 99.9 | RR |
| 24 | IIa | — | Trans-stilbene | 6 | 93 | — | — |

[a]Equivalent weight ratio of the reactants = olefin: osmium: cinchona alkaloid = 1:0.02:0.02, reaction temperature 25° C.
[b]Yield percent after the separation by using column chromatography.
[c]% e.e.(e.e. means enantiomeic excess) was determined by chiral HPLC
[d]absolute configuration was compared with the $[\alpha]_D$ values in the literature.

The Main Advantages of the Present Invention are:

1. A novel and ecofriendly process for asymmetric dihydroxylation of olefins is presented.
2. The present process dispenses the use of soluble, toxic osmium tetroxide or potassium osmate dihydrate instead a heterogeneous reusable LDH-osmates are used.
3. LDH-osmates are prepared and used for asymmetric dihydroxylation of olefins as heterogeneous catalysts. The use of heterogeneous LDH-osmates precludes the presence of osmium in traces with product
4. The enantioselectivity and the yields are good.
5. The work-up procedure is simple.
6. The catalyst is subjected to many recycles, which displayed consistent activity.
7. The present process is environmentally safe since there is no disposal problem.
8. The process is economical.

We claim:

1. LDH-osmate useful as a catalyst, of the formula $[M^{II}_{(1-x)}M^{III}_x(OH)_2][OsO_4^{2-}]_{x/2}.zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and $M^{III}$ is a trivalent ion selected from the group consisting of $Al^{3+}$, $Cr^{3+}$, $Mn^{3+}$, $Fe^{3+}$ and $Co^{3+}$, and x is the mole fraction having integral value ranging from 0.2 to 0.33, and z is the number of water molecules and ranges from 1 to 4.

2. A process for the preparation of the catalyst LDH-osmate of the formula $[M^{II}_{(1-x)}M^{III}_x(OH)_2][OsO_4^{2-}]_{x/2}.zH_2O$ wherein the said process comprises reacting potassium osmate of formula $K_2OsO_4 2H_2O$ with a LDH of formula $[M^{II}_{(1-x)}M^{III}_x(OH)_2][A^{n-}]_{x/n}.zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and $M^{III}$ is a trivalent ion selected from the group consisting of $Al^{3+}$, $Cr^{3+}$, $Mn^{3+}$, $Fe^{3+}$ and $Co^{3+}$ and $A^{n-}$ is an interstitial anion selected from nitrate, carbonate and chloride, x is the mole fraction having integral value ranging from 0.2 to 0.33, and z is the number of water molecules and ranges from 1 to 4, in an aqueous solvent at a temperature ranging between 20 to 30° C. for a period of 5 to 24 h under the nitrogen atmosphere followed by washing to obtain the desired catalyst.

3. A method for the preparation of vicinal diols using the recyclable catalysts LDH-osmates of the formula $[M^{II}_{(1-x)}M^{III}_x(OH)_2][OsO_4^{2-}]_{x/2}.zH_2O$ wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$; $M^{III}$ is a trivalent ion selected from the group consisting of $Al^{3+}$, $Cr^{3+}$, $Mn^{3+}$, $Fe^{3+}$ and $Co^{3+}$ and z is the number of water molecules in catalytic amounts by dihydroxylation of olefins employing an oxidant in a solvent selected from water, acetone, acetonitrile, t-butanol and a mixture thereof at a temperature in the range of −20 to +100° C. for a period of 0.5 to 24 h, and obtaining the pure product vicinal diol.

4. A process for the preparation of chiral vicinal diols using the recyclable catalyst LDH-osmates of the formula $[M^{II}_{(1-x)}M^{III}_x(OH)_2][OsO_4^{2-}]_{x/2}.zH_2O$, wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$; $M^{III}$ is a trivalent ion selected from the group consisting of $Al^{3+}$, $Cr^{3+}$, $Mn^{3+}$, $Fe^{3+}$ and $Co^{3+}$; and x is the mole fraction having integral value ranging from 0.2 to 0.33, and z is the number of water molecules and ranges from 1 to 4, in catalytic amounts by asymmetric dihydroxylation of olefins employing an oxidant in the presence of a cinchona alkaloid compound and a chiral ligand in a solvent selected from water, acetone, acetonitrile, t-butanol and a mixture thereof at a temperature in the range of −20 to +100° C. for a period of 0.5 to 24 h, and obtaining the pure product of chiral vicinal diol.

5. A catalyst as claimed in claim 1 wherein the osmium content ranges between 5 to 30%.

6. A process as claimed in claim 2 wherein said LDH-osmate is prepared from (1) LDH of formula $[M^{II}_{(1-x)}M^{III}_x(OH)_2][A^{n-}]_{x/n} \cdot zH_2O$, wherein $M^{II}$ is a divalent cation selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$; $M^{III}$ is a trivalent ion selected from the group consisting of $Al^{3+}$, $Cr^{3+}$, $Mn^{3+}$, $Fe^{3+}$ and $Co^{3+}$ and $A^{n-}$ is an interstitial anion selected from the; group consisting of chloride, nitrate, carbonate, sulfate, x is the mole fraction having integral value ranging from 0.2 to 0.33, and z is the number of water molecules and ranges from 1 to 4, or (2) calcination of LDH at temperatures in the range of 350 to 550° C.

7. A process as claimed in claim 4 wherein the quantity of LDH-osmate used in the reaction is 0.01 to 3 mol % of osmium content with respect to the substrate.

8. A process as claimed in claim 4 wherein LDH-osmate is recovered by simple filtration and reused for several cycles with consistent activity.

9. A process as claimed in claim 4 wherein the oxidant used is selected from the known group consisting of N-methylmorpholine N-oxide (NMO), Trimethylamine N-oxide, hydrogen peroxide, t-butyl hydrogen peroxide, potassium ferricyanide, sodium periodate or molecular oxygen.

10. A process as claimed in claim 4 wherein the chiral ligand is selected from the group consisting of monomeric or polymeric, hydroquinone 1,4-phthalazinediyl diether, hydroquinidine 2,5-diphenyl-4,6-pyrimidinediyl diether, hydroquinidine (anthraquinone-1,4-diyl) diether, hydroquinidine acetate, O-(4chlorobenzoyl) hydroquinidine, hydroquinidine 9-phenanthryl ether, hydroquinidine 4-methyl-2quinolyl ether and other pseudoenantiomeric forms of these ligand.

* * * * *